United States Patent [19]

Clayman et al.

[11] Patent Number: 5,037,379
[45] Date of Patent: Aug. 6, 1991

[54] SURGICAL TISSUE BAG AND METHOD FOR PERCUTANEOUSLY DEBULKING TISSUE

[75] Inventors: Ralph V. Clayman, Clayton, Mo.; Edward D. Pingleton, Fillmore, Ind.

[73] Assignee: Vance Products Incorporated, Spencer, Ind.

[21] Appl. No.: 543,680

[22] Filed: Jun. 22, 1990

[51] Int. Cl.$^5$ .............................................. A61F 13/00
[52] U.S. Cl. ...................................... 600/37; 604/27; 128/849; 128/85 D; 128/DIG. 24
[58] Field of Search ............... 128/849, 850, 851, 157, 128/155, 161, 162, DIG. 24, 749, 897, 898; 383/71, 72, 109, 113, 123; 600/37; 604/27; 606/151, 28

[56] References Cited

U.S. PATENT DOCUMENTS

| | | | |
|---|---|---|---|
| 2,043,782 | 6/1936 | Sprosty | 383/109 X |
| 4,217,890 | 8/1980 | Owens | 600/37 |
| 4,428,375 | 1/1984 | Ellman | 606/151 |
| 4,576,844 | 3/1986 | Murray et al. | 383/109 X |
| 4,925,711 | 5/1990 | Akao et al. | 383/109 X |

OTHER PUBLICATIONS

Davol Rubber Co. Catalogue, 1959, p. 24.

Primary Examiner—Robert A. Hafer
Assistant Examiner—Brian E. Hanlon
Attorney, Agent, or Firm—Richard J. Godlewski

[57] ABSTRACT

A surgical tissue bag for percutaneously debulking large volumes of tissue contained within the bag. The tissue bag comprises two layers of material, an inner layer of a puncture-resistant material and an outer layer of moisture-proof material for containing cells and fluid therein. The bag material is foldable and flexible for insertion through an access sheath into the surgical site and for forming a gas-tight seal when extended through the access sheath or puncture site. A drawstring is attached to the open end of the bag to close the bag when the tissue is contained therein and pulled through the puncture site in the outer surface of the skin. After the closed open end of the bag is pulled through the puncture site, the closed end is fanned out against the outer layer of the skin, and a morcellator is inserted into the bag for debulking the large volume of tissue. The open end of the bag is continually fanned out to maintain a compact and tight containment of the tissue and fluid remaining in the bag. The morcellation process is continued until the entire volume of tissue is removed at which time the remaining portion of the bag is completely removed from the surgical site area.

21 Claims, 5 Drawing Sheets

SURGICAL TISSUE BAG AND METHOD FOR PERCUTANEOUSLY DEBULKING TISSUE

TECHNICAL FIELD

This invention relates to surgical containment apparatus and, in particular, a surgical tissue bag and method for percutaneously debulking tissue during a minimally invasive surgical procedure.

BACKGROUND OF THE INVENTION

One major problem associated with many minimally invasive endoscopic surgical procedures is the removal of large volumes of tissue through an access sheath. These minimally invasive surgical procedures typically utilize access sheaths having inner diameters ranging in size from 5 mm to 20 mm. Surgical instruments, as well as an endoscope, are inserted through these access sheaths to the surgical site. For example, when surgery is performed within the peritoneal cavity, the cavity is insufflated with a gas to permit viewing of the surgical site as well as provide room in which to manipulate the surgical instruments. As a result, valves or other sealing devices are utilized with these access sheaths to prevent deflation of the peritoneal cavity.

During these minimally invasive endoscopic procedures, it is common that a cyst, tumor, or other affected tissue or organ must be removed through these access sheaths. When the volume of the tissue is small with respect to the access sheath, removal is relatively straightforward. However, when large volumes of tissue must be removed, the use of debulking instruments such as a morcellator are utilized to reduce the size of the tissue by removing small portions thereof through the access sheath. A number of manually operated morcellators are presently available for morcellating or debulking tissue. However, such devices are typically inefficient and require extensive periods of time to remove a large volume of tissue through the access sheath.

Another problem associated with the debulking, removal or morcellation of large tissue volumes is the concern for containing malignant or pathogenic tissue. The morbidity of patients significantly increases when malignant cells of such large volume tissue are permitted to come in contact with surrounding healthy tissue. A malignancy would typically indicate a more invasive procedure in which the cavity is opened and the affected tissue is removed. These invasive open cavity procedures increase the recovery period of the patient and subject the patient to additional discomfort and complications.

As a result, the debulking of large malignant tissue volumes percutaneously through an access sheath presents significant morbidity risks to the patient. Only when other complicating factors are involved is the debulking of large malignant tissue volumes even indicated.

SUMMARY OF THE INVENTION

These problems are overcome and a technical advantage is achieved by a surgical tissue bag and method for percutaneously debulking tissue while containing the tissue and preventing the spread of malignant cells to healthy tissue. The flexible material bag advantageously effects and maintains a gas-tight seal when the bag traverses the percutaneous puncture site. The flexible material bag compliantly plugs the puncture site, thus preventing any significant loss of body cavity insufflating gas.

The tissue bag comprises first and second layers of material that are flexible and foldable for percutaneous insertion through an access sheath during the minimally invasive surgical procedure. The inner layer comprises a puncture-resistant material for advantageously resisting penetration by a surgical morcellating instrument and particularly one with an open-ended cutting edge. The second layer comprises a moisture proof material for containing the tissue within the bag and preventing the transmission of fluids or tissue cells to healthy tissue within the surgical site.

In one illustrative embodiment, the two layers comprise a single sheet having opposite first and second ends folded back to contact each other and form a folded side of the bag. The first and second folded-back ends are attached together to form a second side of the bag. The sheet also has opposite first and second sides each folded back on itself, the facing portions of the first folded-back side being attached together between the folded and second sides of the bag to form the closed end of the bag. The second folded-back side forms the open end of the bag. The bag also includes a drawstring attached about the open end thereof and having a length extendable through the access sheath during the surgical procedure for drawing the open end of the bag closed. The folded side of the bag advantageously causes the open end of the bag to open for receiving tissue once inserted through the access sheath into the body cavity.

The tissue bag also includes an adhesive material affixing the first and second folded-back ends of the sheet together as well as affixing the facing portions of the first folded-back side of the bag together. In another embodiment, the layers of the sheet may be laminated together along with the folded-back side of the bag. In a third embodiment, the tissue bag utilizes a thread affixing opposite end and the folded-back side together.

In the illustrative embodiment, the puncture-resistant material comprises nylon, whereas the moisture-proof material comprises a plastisol coating integrally bonded together or laminated to form a single sheet of the bag.

In the alternative embodiment of the tissue bag, an inner bag comprising a sheet of the puncture-resistant material is formed and positioned within an outer bag comprised of the moisture-proof material. The inner and outer bags each include a sheet of the respective puncture-resistant and moisture-proof material of which the first and second opposite ends thereof are folded back on each other to form a folded side of the bag and are attached together to form a second side of the bag. Facing portions of the folded-back side of the sheets are attached together between the folded and second sides of the bag for forming the closed end of the bag. The inner bag is positioned within the outer bag. A drawstring is attached about both open ends of the inner and outer bags and has a length extendable through the sheath during the surgical procedure for drawing the open end closed.

The method of percutaneously debulking tissue basically comprises inserting percutaneously the surgical tissue bag through an access sheath into a body cavity and positioning tissue in the bag through the open end thereof. The method also includes pulling the closed open end of the tissue bag out of the body cavity and morcellating or debulking the tissue through the open end with the tissue and the rest of the bag remaining in the body cavity.

The surgical procedure initially comprises percutaneously inserting an access sheath into the body cavity and inserting the tissue bag into the body cavity with the drawstring extending externally through the access sheath. When positioned in the body cavity, the large volume tissue is inserted in the bag, and the drawstring is pulled to close the bag around the tissue. The closed tissue bag is then drawn against the distal end of the access sheath and pulled out of the body cavity with the access sheath. The flexible material bag advantageously maintains a gas-tight seal, thus preventing any significant loss of cavity insufflating gas. The access sheath is removed from the around drawstring and the closed open end of the tissue bag is opened and fanned out against the outside surface of the body to permit entry of the morcellator through the open end of the bag.

A morcellator then debulks and removes segments of the tissue through the open end in the bag extending into the body cavity. As segments of the tissue are removed with the morcellator, the bag is further extracted from the body cavity to advantageously maintain a tight containment of the remaining tissue in the bag. This advantageously stabilizes the organ or tissue by reducing the bag volume as the morcellation proceeds and leads toward controlled removal of the tissue and the bag from the body cavity. Containment of the tissue within the bag also prevents the spread of malignant cells to healthy tissue in the body cavity.

DETAILED DESCRIPTION

Figure 1A:
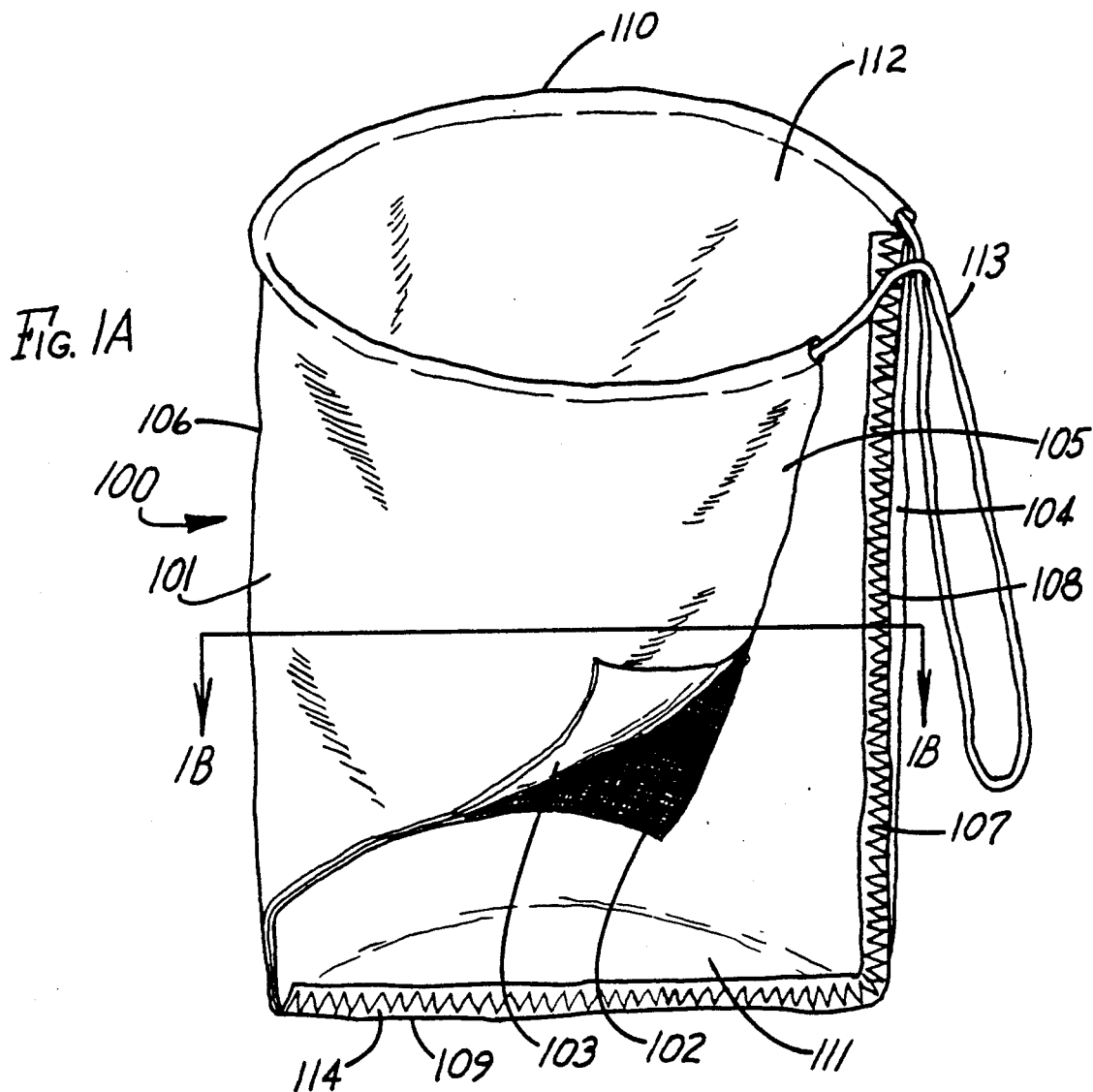
FIG. 1A depicts a single sheet surgical tissue bag of the present invention.

Depicted in FIG. 1A is a surgical tissue bag 100 for percutaneously debulking tissue contained therein and preventing the spread of malignant cells to healthy tissue within a surgical site. The tissue bag is comprised of a flexible and foldable material for insertion into a body cavity through an access sheath inserted into the cavity for a minimally invasive surgical procedure. The flexible material bag effects and maintains a gas-tight seal while traversing the percutaneous puncture site. The flexible material also compliantly plugs the puncture site, thus preventing any significant loss of body cavity insufflating gas.

The tissue bag comprises a sheet 101 of material having two layers 102 and 103 for containing the tissue or organ therein. The inner layer 102 comprises a puncture-resistant material such as nylon in either a woven, as shown, or solid layer form for resisting penetration by a surgical morcellating instrument. Outer layer 103 comprising a moisture-proof material such as a plastisol has been peeled away to view the inner puncture-resistant material layer 102. A moisture-proof material layer prevents the transmission of fluid or malignant tissue cells to healthy tissue within the surgical site. The two layers have been formed or laminated together to form single sheet 101 having opposite first and second ends 104 and 105 folded back on each other to form folded side 106 of the bag.

Figure 1B:
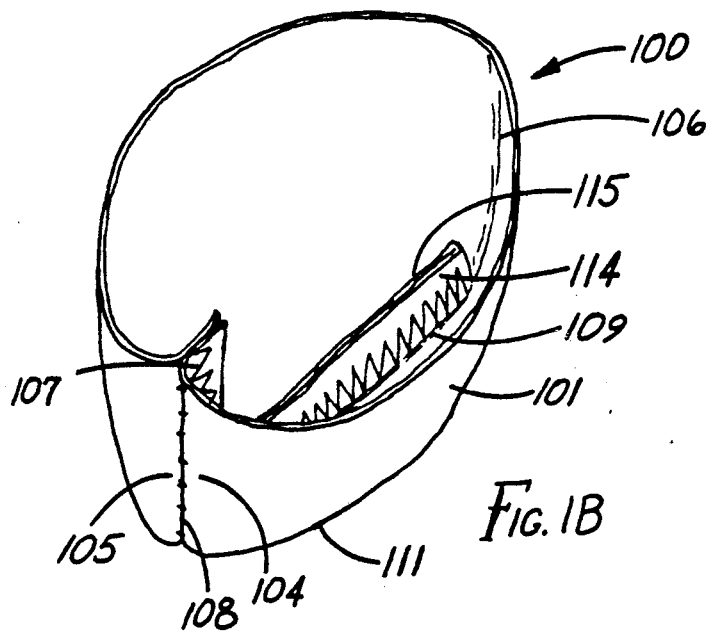
FIG. 1B depicts a top view into the bag of FIG. 1A along the line 1B—1B.

Depicted in FIG. 1B is top view of bag 100 of FIG. 1A along the line 1B—1B to better visualize the various sheet ends, sides, and attachments thereof. The first and second folded-back ends of the sheet are attached together using any one of a number of well-known means of attachment such as an adhesive, a vulcanization or lamination or, as shown, a thread-like material 107 to attach the folded-back ends together which forms seamed second side 108 of the bag. Sheet 101 also has opposite sides 109 and 110 with each side folded back on itself. The facing portions 114 and 115 of folded-back side 109 are attached together between the folded and second sides of the bag to form seamed closed end 111 of the bag. The second folded-back side 110 of the sheet forms open end 112 of the bag.

The tissue bag also includes closure means such as a loop drawstring 113 attached in a well-known manner about the open end 112 of the bag and has a portion extending from the open end and having a length extendable through an access sheath during the surgical procedure for drawing the open end of the bag closed and pulling the closed open end of the bag from the cavity and through the puncture site. Folded side 106 of the bag causes open end 112 of the bag to open for receiving tissue once the bag has been inserted through the access sheath into the body cavity. The color of the bag is also preferably opaque to prevent glare to the endoscopist.

Figure 2:
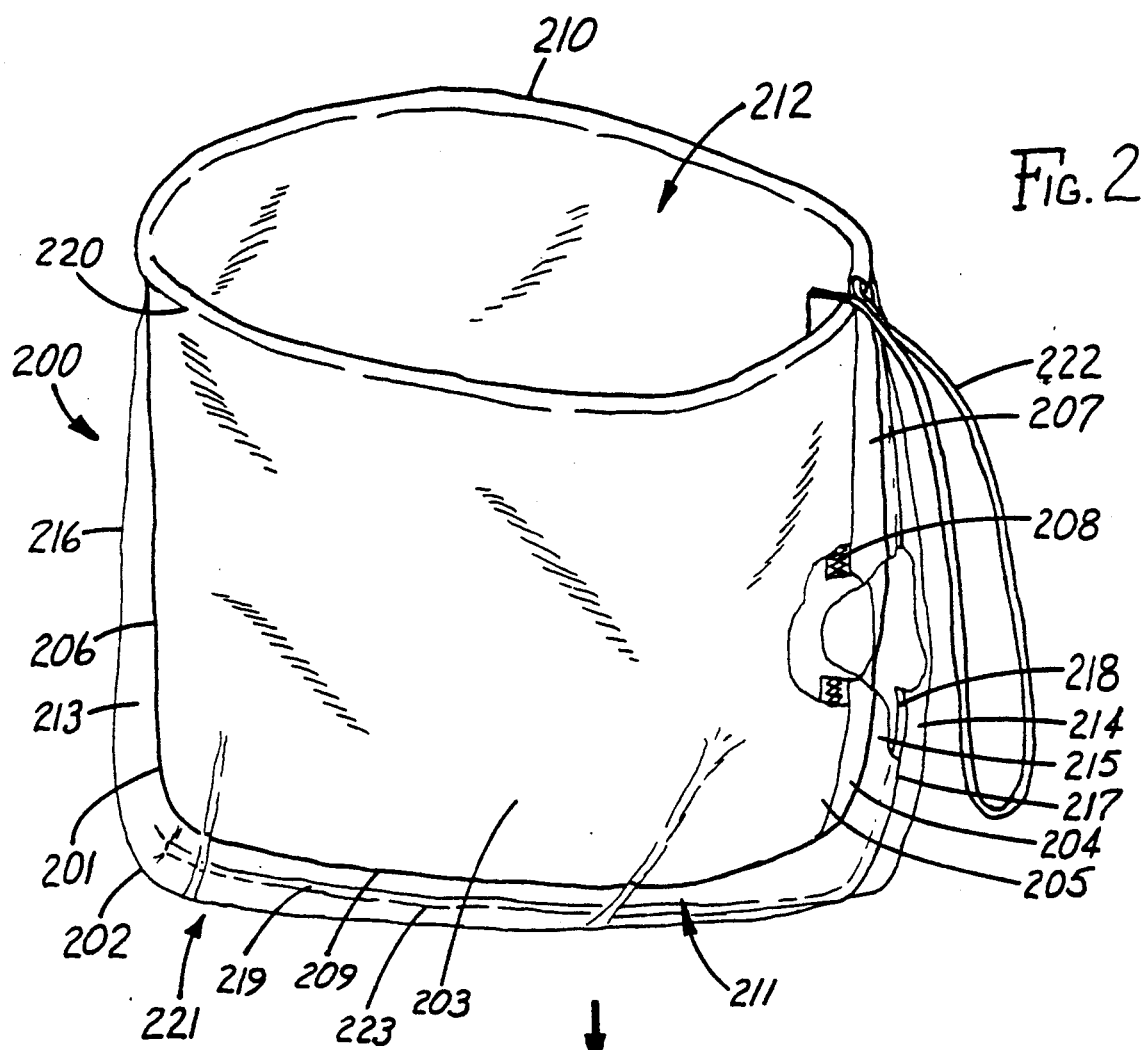
FIG. 2 depicts another embodiment of the surgical tissue bag having two separate layers to form an inner and an outer bag.

Depicted in FIG. 2 is surgical tissue bag 200 which includes an inner bag 201 and an outer bag 202 for percutaneously debulking tissue while containing the tissue and preventing the spread of malignant cells or fluid to healthy tissue. Tissue bag 200 includes two separated layers of material to form the inner and outer bags. The single layer bags are made of material that is both flexible and foldable for percutaneous insertion through an access sheath during a minimally invasive surgical procedure. The inner bag comprises a puncture-resistant material for resisting penetration by a surgical morcellating instrument, whereas the outer bag comprises a moisture-proof material for preventing the transmittal of fluid or tissue cells to healthy tissue within the surgical site. The two flexible material layers of the bag also effect and maintain a gas-tight seal when traversing the puncture site.

Inner bag 201 includes a sheet 203 of puncture-resistant material having opposite ends 204 and 205 folded back on each other to form a folded side 206 of the inner bag and are attached together to form a seamed second side 207 of the inner bag. Opposite ends 204 and 205 of the inner bag are attached together using a thread-like material 208 or any other well-known fastening material or process as shown in the partial cut-away view. As previously described, these ends may be glued, laminated, or vulcanized depending on the type of puncture-resistant material utilized. Sheet 203 also includes opposite sides 209 and 210 with each side folded back on itself. The facing portions of folded-back side 209 are attached together to form the seamed closed end 211 of the inner bag. Folded-back side 210 forms the open end 212 of the inner bag.

Outer bag 202 includes a sheet 213 of moisture-proof material. Similar to sheet 203, outer sheet 213 has opposite first and second ends 214 and 215 folded back on each other to form folded side 216 of the outer bag. Folded back ends 214 and 215 are attached together to form a seamed second side 217 of the outer bag and are attached together using a suitable fastening material 218, as shown in the partial cut-away view, such as thread, glue, and the like or fastened with the use of a suitable bonding process. Opposite sides 219 and 220 of the sheet are each folded back on itself. The facing portions of folded-back side 219 are attached together using suitable fastening means 223 to form the seamed closed end 221 of the outer bag. The second folded-back side 220 of the sheet forms the open end of the outer bag. The open ends of the inner and outer bags are attached together and a drawstring 222 attached in a well-known manner thereabout, which is pullable around the open ends thereof. The drawstring has a length extendable through an access sheath during the surgical procedure for drawing the open ends of the two bags closed.

Figure 3:
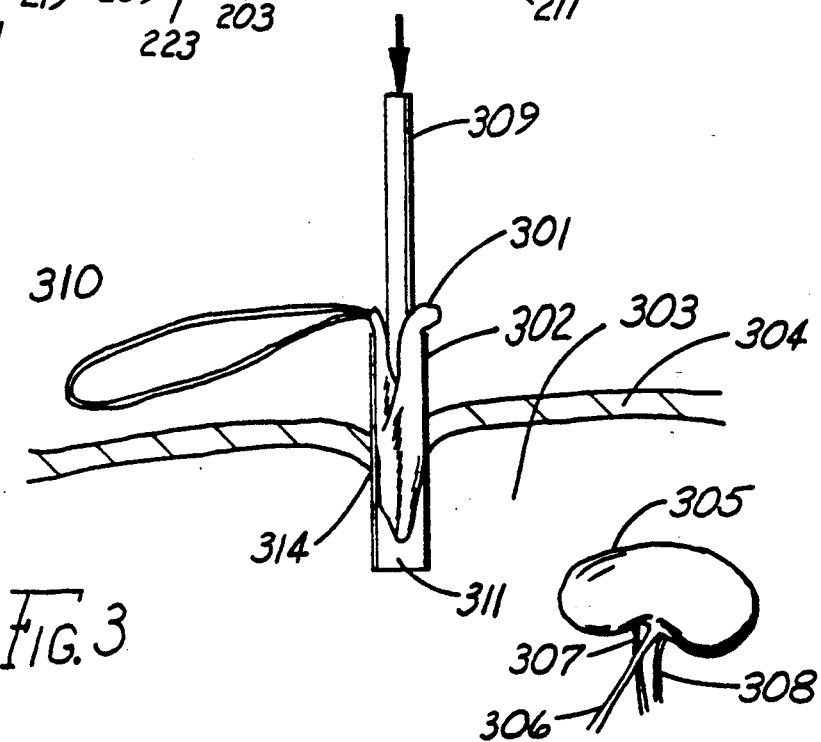
FIGS. 3-9 depict the method for percutaneously debulking tissue contained within the surgical tissue bag of FIG. 1A inserted during a minimally invasive surgical procedure.

Depicted in FIGS. 3-9 is the method of percutaneously debulking tissue in tissue bag 301 through an access sheath 302 that is inserted through a puncture site 314 into body cavity 303. As depicted in FIG. 3, access sheath 302 is pushed into peritoneal cavity 303 through outer layers of tissue 304 such as skin, muscle, fat, etc. This is a well-known surgical procedure utilizing a trocar sheath. The illustrative surgical procedure utilized will be directed to a nephrectomy in which kidney 305 of the patient is percutaneously cut from connective tissue, and each of artery 306, vein 307, and ureter 308 is severed between surgical clips to prevent leakage of blood and urine into the cavity. After the trocar sheath 302 has been inserted into the peritoneal cavity 303, tissue bag 301 is folded and inserted through passageway 311 of the trocar sheath with a blunt tip push rod 309 into peritoneal cavity 303.

Figure 4:
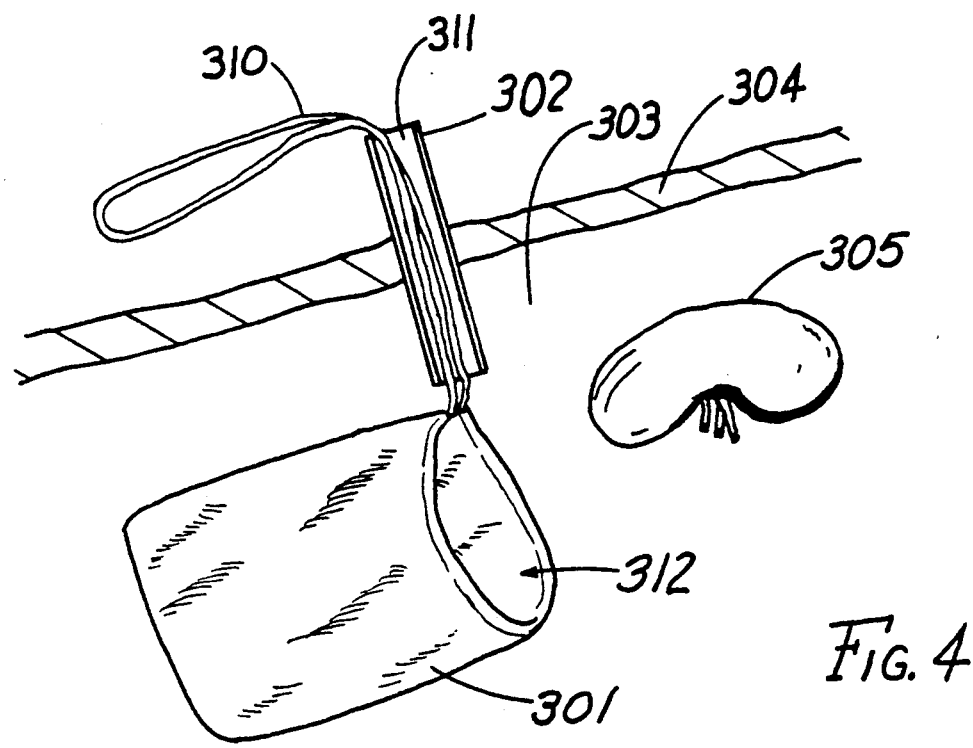
Figure 5:
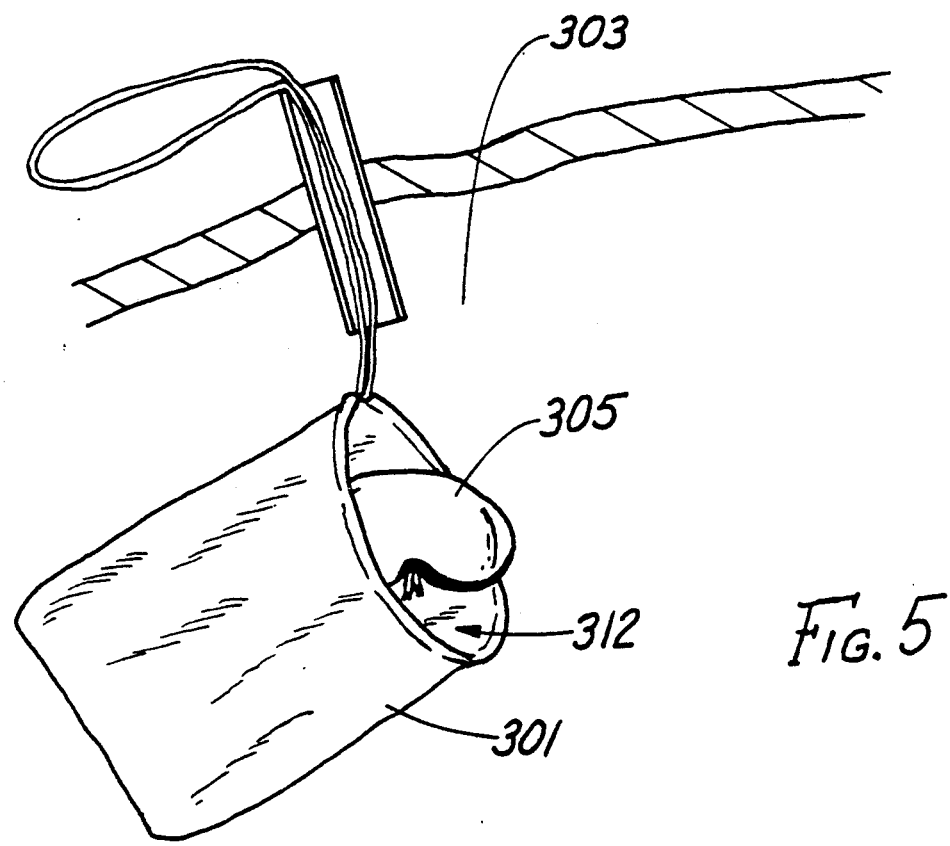

As depicted in FIG. 4, drawstring 310 extends from the tissue bag in the peritoneal cavity through passageway 311 of the trocar sheath and external to the patient for subsequently closing the open end 312 of the bag. The bag has been folded as previously described such that when introduced into the insufflated peritoneal cavity, the bag will readily open or with minimal assistance with an endoscopic instrument that is inserted through another trocar sheath (not shown). Although tissue bag 301 has been described as including a folded side for opening the open end, the bag may also be formed with an open end such as in a molding or an injection molding process. After insertion through the trocar sheath, the molded open end will return to its' original size. After tissue bag 301 has been inserted into the peritoneal cavity 303, kidney 305 is inserted into the open end 312 of the tissue bag as depicted in FIG. 5.

Figure 6:
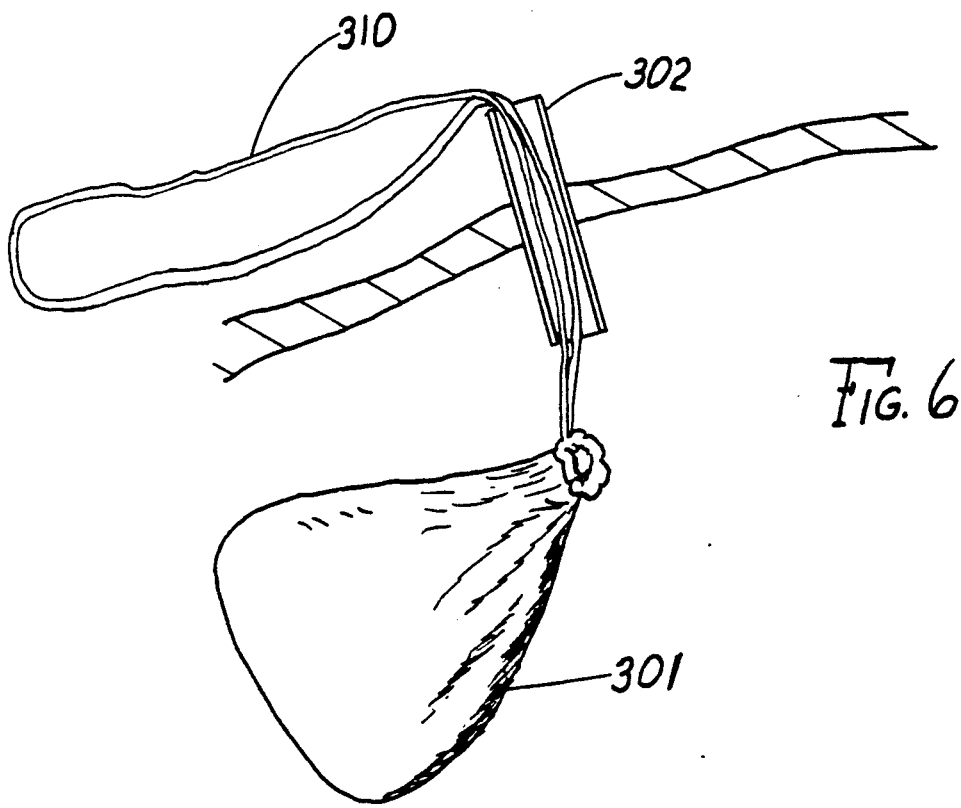
Figure 7:
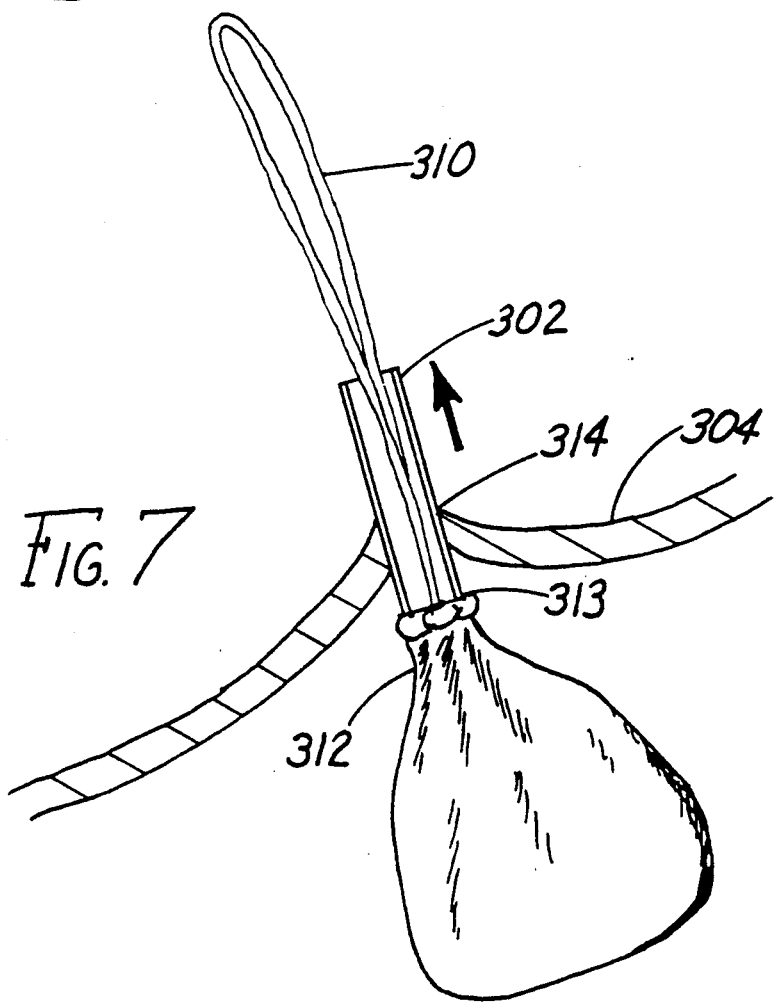

After kidney 305 is placed entirely within the tissue bag, drawstring 310 is externally pulled through the trocar sheath to close the open end of tissue bag 301 as depicted in FIG. 6. The drawstring is further pulled to bring the closed open end of the bag against the distal end 313 of trocar sheath 302 as depicted in FIG. 7. Tension is applied to the drawstring to pull the closed open end 312 of the tissue bag and the trocar sheath through the opening 314 of the outer tissue layers 304.

Figure 8:
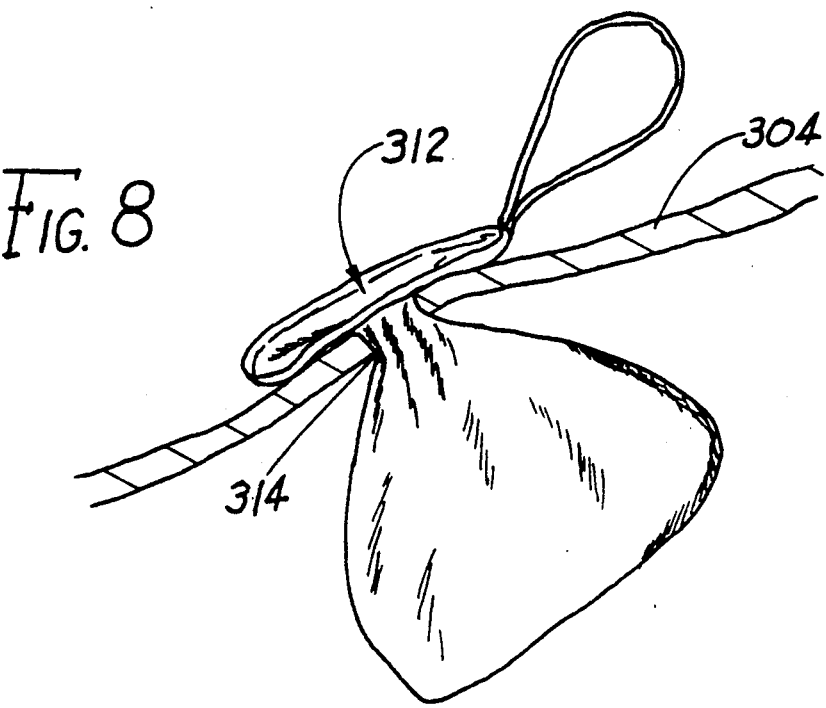

After the closed open end is pulled through puncture site 314 of the outer tissue layers 304, the trocar sheath is removed from the drawstring, and the closed open end is opened and fanned out against the outer layer of the skin as depicted in FIG. 8. When positioned through the puncture site, the flexible material bag maintains a gas-tight seal to prevent any significant loss of body cavity insufflating gas.

Figure 9:
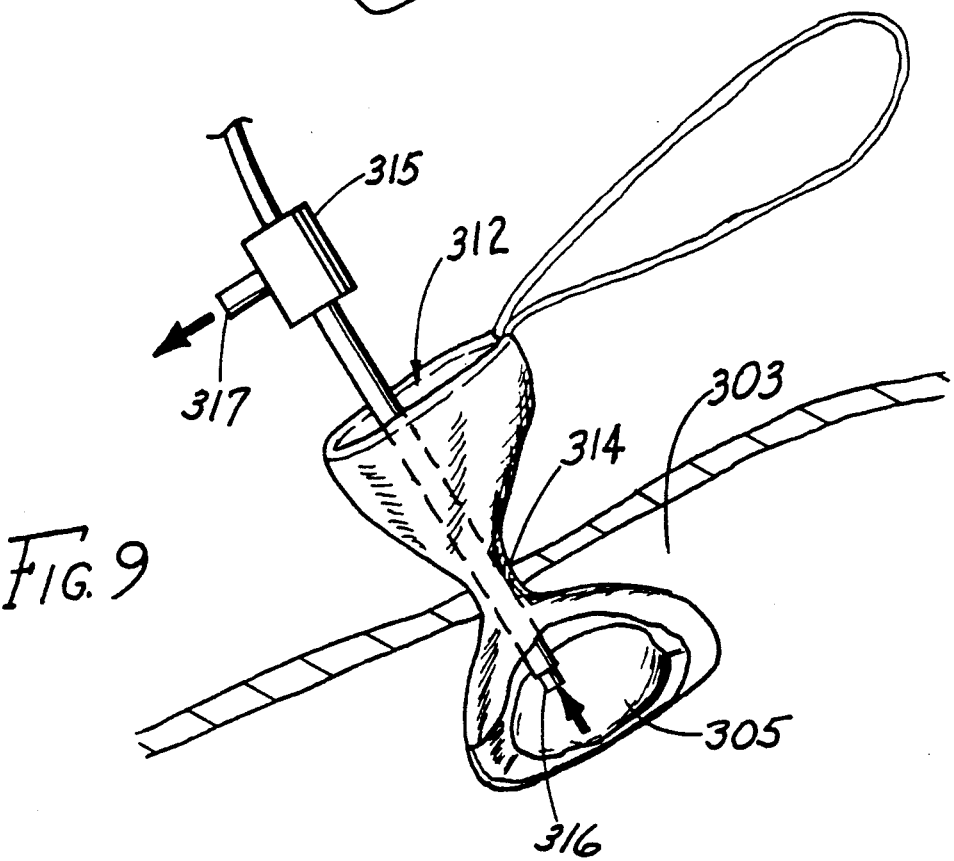

As depicted in FIG. 9, an open-ended morcellator 315 is then inserted through open end 312 of the bag to debulk kidney 305 which remains in the peritoneal cavity along with the distal end of the tissue bag. A morcellator for this purpose is described in U.S. patent application of one of the present inventors filed concurrently herewith. The morcellator includes a rotary cutting tube 316 which cuts and suctions segments or pieces of the kidney externally through a vacuum port 317. The debulking process is continued until the entire kidney has been removed from the tissue bag. The puncture-resistant layer of the bag prevents the morcellator from cutting through the bag and into the peritoneal cavity 303, spilling possibly malignant cells and fluid into the cavity. As the kidney is debulked, the open end of the bag is continued to be pulled out of puncture site 314 of the tissue to keep a tight compact volume in which the morcellator may cut and remove the remaining portions of the kidney.

It is to be understood that the above-described surgical tissue bag and method for percutaneously debulking a large volume of tissue is merely illustrative, and that other tissue bags and methods may be devised by those skilled in the art without departing from the spirit and scope of this invention. In particular, the surgical tissue bag may be formed from molded or injection-molded material having both moisture-proof and puncture-resistant qualities and/or layers. The bag material would be flexible and foldable enough to insert through the trocar sheath but yet readily open upon insertion into the surgical site cavity during the minimally invasive endoscopic procedure. The flexible material of the bag would also maintain a gas-tight seal when positioned through the puncture site. The surgical bag advantageously contains the cells therein to minimize contamination of the surgical site. The method of percutaneously debulking a large volume tissue also contemplates pulling the closed open end of the surgical tissue bag entirely through the hollow passageway of the trocar sheath. Other means of drawing the open end of the tissue bag are also contemplated.

What is claimed is:

1. A minimally invasive surgical tissue bag for percutaneously debulking tissue, comprising:

a sheet having first and second layers of dissimilar material, said first layer comprising a puncture-resistant material, said second layer comprising a moisture-proof material, said first and second layers being flexible and foldable for percutaneous insertion through an access sheath during a minimally invasive surgical procedure, said sheet having opposite first and second ends folded back on each other and forming a folded side of said bag, said first and second folded-back ends being affixed together and forming a second side of said bag, said sheet also having opposite first and second sides, each side being folded back on itself, facing portions of said first folded-back side being attached together between said folded and second sides of said bag and forming a closed end of said bag, said second folded-back side forming an open end of said bag; and a drawstring attached about said open end of said bag and having a length extendable through said sheath during said surgical procedure for drawing said open end closed.

2. The tissue bag of claim 1 further comprising an adhesive material affixing said first and second folded-back ends of said sheet together and affixing said facing portions of said first folded-back side together.

3. The tissue bag of claim 1 wherein said first and second folded-back ends of said sheet are laminated together and wherein said facing portions of said first folded-back side are laminated together.

4. The tissue bag of claim 1 further comprising a thread affixing said first and second folded-back ends of said sheet together and affixing said facing portions of said first folded-back side together.

5. The tissue bag of claim 1 wherein said puncture-resistant material has a melting temperature higher than that of said moisture-proof material.

6. The tissue bag of claim 1 wherein said moisture-proof material comprises a plastisol.

7. The tissue bag of claim 1 wherein said first and second layers are laminated together.

8. The tissue bag of claim 1 wherein said first and second layers are integrally bonded together.

9. The tissue bag of claim 1 wherein at least one of said first and second layers is opaque.

10. A minimally invasive surgical tissue bag for percutaneously debulking tissue, comprising:
an inner bag comprising a first sheet of puncture-resistant material having opposite first and second ends folded back on each other and forming a folded side of said inner bag, said first and second folded-back ends being attached together and forming a second side of said inner bag, said first sheet also having opposite first and second sides each folded back on itself, facing portions of said first folded-back side being attached together between said folded and second sides of said inner bag and forming a closed end of said inner bag, said second folded-back side forming an open end of said bag;
an outer bag having said inner bag positioned therein and comprising a second sheet of moisture-proof material dissimilar from said puncture-resistant material and having first and second ends folded back on each other and forming a folded side of said outer bag, said first and second folded-back ends of said second sheet being attached together and forming a second side of said outer bag, said second sheet also having opposite first and second sides each folded back on itself, facing portions of said first folded-back ends of said second sheet being attached together between said folded and second sides of said outer bag, said second folded-back side of said second sheet forming an open end of said outer bag; said first and second sheets being flexible and foldable for percutaneous insertion through an access sheath during a minimally invasive surgical procedure; and
a drawstring attached about said open ends of said inner and outer bags and having a length extendable through said sheath during said surgical procedure for drawing said open end closed.

11. The tissue bag of claim 10 wherein said puncture-resistant material comprises nylon.

12. The tissue bag of claim 11 wherein said moisture-proof material comprises a plastisol.

13. The method of percutaneously debulking tissue, comprising:
inserting percutaneously a tissue bag through an access sheath into a body cavity, said tissue bag comprising: a sheet having first and second layers of dissimilar material, said first layer comprising a puncture-resistant material, said second layer comprising a moisture-proof material, said first and second layers being flexible and foldable for percutaneous insertion through an access sheath during a minimally invasive surgical procedure, said sheet having opposite first and seconds ends folded back on each other and forming a folded side of said bag, said first and second folded-back ends being affixed together and forming a second side of said bag, said sheet also having opposite first and second sides, each side being folded back on itself, facing portions of said first folded-back side being attached together between said folded and second sides of said bag and forming a closed end of said bag, said second folded-back side forming an open end of said bag; and a drawstring attached about said open end of said bag and having a length extendable through said sheath during said surgical procedure for drawing said open end closed;
positioning said tissue in said bag through an open end thereof;
pulling said open end of said tissue bag out of said body cavity; and
morcellating through said open end said tissue in said bag in said body cavity.

14. The method of claim 13 further comprising inserting percutaneously said access sheath into said body cavity.

15. The method of claim 13 positioning the drawstring attached about said open end of said tissue bag through said access sheath.

16. The method of claim 13 wherein said pulling includes positioning the drawstring attached about said open end of said tissue bag through said access sheath and closing said open end of said tissue bag with said drawstring.

17. The method of claim 16 wherein said pulling further includes pulling said closed open of said tissue bag and said access sheath out of said body cavity.

18. The method of claim 17 further comprising opening outside of said body cavity said closed open end of said bag.

19. The method of claim 18 pulling the remaining portion of said bag out of said cavity as said tissue is morcellated.

20. The method of claim 13 wherein said morcellating includes percutaneously inserting a morcellator through said open end of said bag into said tissue and removing said tissue in said bag through said morcellator.

21. A minimally invasive surgical tissue bag for percutaneously debulking tissue, comprising:
a first layer of puncture-resistant material having flexible and foldable properties for insertion through an access sheath during a minimally invasive surgical procedure into a body cavity and formed into a predetermined shape having an opening therein for containment therein of tissue within said body cavity;
a second layer of moisture-proof material dissimilar from said puncture-resistant material having flexible and foldable properties for insertion through said access sheath and formed into said predetermined shape having said opening therein; and
closure means attached about said open ends of said layers for closing said openings through said access sheath and having a portion extendable through said access sheath for pulling said closed openings from said body cavity during said minimally invasive surgical procedure.

* * * * *